US005208465A

United States Patent [19]

Jacobson

[11] Patent Number: 5,208,465

[45] Date of Patent: May 4, 1993

[54] AUTOMATIC DETECTION SYSTEM OF OIL SPILLAGE INTO SEA WATERS

[75] Inventor: Amnon Jacobson, Tel Aviv, Israel

[73] Assignee: Ispra - Israel Product Research Company Ltd., Herzlia, Israel

[21] Appl. No.: 823,832

[22] Filed: Jan. 22, 1992

[51] Int. Cl.[5] .............................................. G01N 15/06

[52] U.S. Cl. .................................... 250/573; 356/442

[58] Field of Search ........ 250/573, 574, 576, 901–903, 250/227.28, 227.31, 227.32; 73/293, 305, 307; 356/133, 135, 436, 440–442

[56] References Cited

U.S. PATENT DOCUMENTS

| | | | |
|---|---|---|---|
| 4,320,291 | 3/1982 | Uramoto | 250/903 |
| 4,342,919 | 8/1982 | Brogardh | 73/293 |
| 4,544,840 | 10/1985 | Keller | 250/573 |
| 4,711,126 | 12/1987 | Houpt et al. | 356/133 |
| 4,719,359 | 1/1988 | Rose | 356/436 |
| 4,876,888 | 10/1989 | Ricketts et al. | 73/305 |
| 4,882,499 | 11/1989 | Luakkala et al. | 73/293 |
| 4,893,935 | 1/1990 | Mandel et al. | 356/436 |
| 4,936,681 | 6/1990 | Ruhrmann | 356/133 |
| 4,940,902 | 7/1990 | Mechalas et al. | 250/573 |

*Primary Examiner*—David C. Nelms
*Assistant Examiner*—S. Allen
*Attorney, Agent, or Firm*—Charles E. Baxley

[57] ABSTRACT

An automatic detection system for control of oil spillage into sea waters comprising a plurality of optical fiber cables connected each to a control box and to a plurality of sensors located remotedly in the open sea, and each of the sensors is a part of a closed loop of a light signal, transmitted from the control box and received back by it. Each of the sensors consists of a floating buoy affixed to a permanent location in the open sea, having its center of gravity adjustable and stabilized, so that when it floats, the central part of the sensor rests at sea level. The buoy is provided with a central bore, into which the optical fiber cable's ending is positioned; and a plurality of concentric channels are provided from all sides of the bore, leading sea water from the outer surface of the buoy inwards. The optical fiber cable's ending is provided with a light indicator; so that when an oil slick enters the bore, the light parameters' change can be instantaneously detected by the light indicator and the control box set on the alarm.

34 Claims, 2 Drawing Sheets

14
11
12
16A
16
15
10
13
19
18
20

AUTOMATIC DETECTION SYSTEM OF OIL SPILLAGE INTO SEA WATERS

BACKGROUND OF THE INVENTION

This invention relates to an automatic detection system to control the spillage of oil into the sea. The prevention of sea pollution is of great concern to our society. The early detection of leakage of spilled oil, whether from off shore oil drilling platforms or from tankers or from pipelines is a large step towards the prevention of sea pollution.

At this time, no commercial sensors are available which can permanently, automatically and instantaneously detect crude oil floating on the water level and at the same time send an alarm.

The present detection systems are either visual control of sea waters by the port sea control boats or by overhead control form helicopters or airplanes.

An automatic detection system must have the following features:

a) It must be spark free non electric so as to avoid any danger of explosion hazards.

b) The central control box and alarm unit should be installed several kilometers away from the sensor units, which may have to be spread over large areas. The information from the sensors will have to be processed centrally at the control site.

c) The detection capability of the system should not be affected by waves motion.

It is therefore the purpose of this invention to provide a detection system having a plurality of sensor units placed in one or numerous sites in the open sea as required, leading information into a central automatic control box, having zone resolution and electronic processing means, to yield at a short time information on the location and size of the oil pollution spot in the sea, defining the boundaries of the oil spot, so that immediate action can be taken to avoid further spillage.

The detection system herein provided comprises a plurality of optical fiber cables connected each at the first ending to a control box having an electronic processing and alarm means, and a plurality of light transmitters and light detectors connected to said first endings of said optical fiber cables; and the second endings of said fiber cables are connected to a plurality of sensors located remotedly in the open sea; and each of said sensors is a part of a closed loop of a light signal transmitted by one of said light transmitters through one of said optical fiber cable through said sensor, and received by one of said light detectors provided in said control box; and each of said sensors consists of a floating buoy affixed by mechanical means to a permanent location in the open sea, so as to allow said buoy free vertical movement but limit its horizontal movement; and said buoy is constructed of a light weight floatable material, and has its center of gravity adjustable and stabilized by a weight, so that when it floats, the central part of said sensors rests at sea level; and said buoy is provided with a central bore, into which said second optical fiber cable's ending is positioned; and a plurality of concentric channels are provided from all sides of said bore, leading sea water from the outer surface of said buoy inwards; and said second optical fiber cable's ending is terminated in said bore and provided with a light indicator; so that said light signal, transmitted through said optic fiber cable from said light transmitter, passes through said light indicator and when an oil slick enters said bore, the light parameters' change can be instantaneously detected by said light detector and said electronic processing means of said control box set on said alarm means.

The indicator should enable said system to detect changes in the intensity of transmitted and detected light, caused by light absorption and scattering by the oil, or by changes in the refractive index of the waters surrounding the indicator.

In the preferred embodiment said light indicator contains a light intensity sensor, comprising two fiber ends placed one opposite the other in said bore, so that one fiber end is positioned below sea level and the other is placed above sea level; and when said light signal passes through a gap formed between said two fiber ends, light absorption through said oil slick, sea water and air is higher than the light absorbed through the sea water and air only; and said differential light absorption can be instantaneously detected by said light detector.

In another preferred embodiment said light indicator contains a refractive index sensor, comprising a noninsulated optical fiber of said optical fiber cable; said fiber passes in said bore at sea level, and said fiber is coiled around a circular bar and is surrounded with a clad, capable to transmit a light energy, leaking from the core of said optical fiber; and said clad is protected along said coil by a thin metal layer; and said clad changes its light transmission properties according to a refractive index of a surrounding medium; so that, when the surrounding waters are contaminated with organic oils, the refractive index of said surrounding medium increases, thus some of the light power transmitted in said clad is leaked outside said clad and is absorbed by said surrounding medium, hence a reduction of the light power can be instantaneously detected by said light detector.

In one preferred embodiment said optical fiber is made of a plastic clad silica; said plastic clad is removed along said coiled fiber, and said metal layer is applied directly on said silica core.

In the preferred embodiment said metal layer is of platinum, rhodium, gold or palladium.

In the preferred embodiments said light indicator contains both said light intensity sensor, and said refractive index sensor, connected in sequence and acting as amplifyers to each other.

In another preferred embodiment of the invention said optical fiber cable leading from said control box to said light indicator consists of a single fiber, and said light indicator is provided with a reflector located in the water in a position so as to create said gap; and said reflector reflects back into said fiber the light transmitted through said fiber's first end; and on said second end of said fiber an optical coupler is provided transmitting the reflected light beam into a receiver which detects the differential light absorption caused due to interference of an oil slick; and said electronic processing means then set on the alarm.

In another preferred embodiment said reflector is a mirror or an optical prism.

In another preferred embodiment said light indicator does not include any auxiliary optical device, and said fiber ends are spaced at a close distance between each other, the preferred gap should not exceed 100 mms.

In another preferred embodiment at least one of said two fiber ends is connected to a lens which size is preferably adjusted to the numerical aperture of said fiber for the lens to be optimally illuminated.

By using the lenses one overcomes the gap distance limitation, as the loss of light energy caused by water and air is relatively negligible. However, when an oil slick enters the gap between the lenses the differential light absorption by the oil is immediately detected.

In order to overcome the possibility that the light transmitted from the one fiber ending, in the sensor gap, may not enter effectively into the receiving fiber ending; several solutions are herein proposed:

a) In one embodiment said two fiber ends forming the indicator's gap are each connected to a plurality of lenses arranged consequently, so that the light energy transmitted from said one fiber end is collected effectively through the lenses of said other fiber end.

b) In another embodiment said lenses connected on either or both fiber end is so chosen to either have a special curvature, or be constructed from a specific plastic or glass material, or have a specific lens coating which will maximize the light energy transmitted from one lens connected to said one fiber end and received through the other lense connected to said other fiber end in said indicator's gap.

When said lens is located on one end of said fiber only, the light transmitted through said lens reaches the other end of the fiber even if the buoy tilts due to waves motion, and the light beam through said lens is refracted on the surface between the air and the water, so that said fiber end is illuminated even if the tilting angle of said buoy is considerable.

In the preferred embodiment said electronic processing means is provided with software, capable to differentiate light absorption created by the motion of sea waves, and light absorption created by the oil slick, thus providing an accurate control of said alarm means.

In the preferred embodiment said optical fibers are protected in a single or multi cable system.

In one preferred embodiment said cable is a duplex fiber cable, having two fibers only.

In another preferred embodiment said cable is a multiple fiber cable.

In one preferred embodiment said optic fiber cable is made of all glass fiber.

In another embodiment the cable is made of plastic coated glass fiber.

In yet another embodiment the cable is made of all plastic fiber.

The fiber types in all embodiments are either of a single mode or multimode, or step index types.

In the preferred embodiment the cable is a submarine cable type.

In the preferred embodiment the light wavelength applied in said system is about 820 nm.

In the preferred embodiment said light transmitter emits pulsed light with predetermined duration and intervals so that the detection may be recognized efficiently by said electronic processing unit installed in said control box.

In the preferred embodiment said buoy is inserted in a cage which is connected to a fixed structure built out at sea, or is anchored by any commercial anchor means; and said cage affixes said buoy movement allowing it to move vertically free, but limiting its horizontal movement.

In another embodiment said cage is connected to an anchoring mooring buoy.

In the preferred embodiment the floating buoy containing said light indicator has a stainless steel net cover preventing the passage of sea weeds, fish or other solid pollutants into said buoy concentric channels leading to said bore, where said optical fibers are placed.

In the preferred embodiment said buoy is provided with a dispenser releasing a chemical preventing the build up of bacteria or sea weeds in said buoy channels leading to said bore, and on said light indicator's optical surfaces.

In another embodiment said light indicator's optical surfaces are coated with an oil repelling layer (such as Tetrasluoroethylene), repelling oil from sticking to said surfaces.

In the preferred embodiment said buoy is made of foamed light weight material such as cork, or any other foamed plastic material commercially used in sea floats, such as polystyrene, polyurethane, polyethylene or the like, protected by a suitable protective layer, such as paint or a protective chemical varnish.

In the preferred embodiment said buoy is stabilized by fins so that the axis of the light rays transmitted through said fiber ends in said light indicator, are always emitted in an almost perpendicular angle to the water level, regardless of effects by sea waves.

In another preferred embodiment said buoy contains wave breakers in the form of mechanical hurdles which eliminate the surface roughness of the water entering said sensor's gap, thus keeping the water level in said sensor's gap as calm as possible.

The hurdles are so designed as not to interfere with the oil passage through the concentric channels to the sensor's gap.

BRIEF DESCRIPTION OF THE INVENTION

The invention can be best described by the aide of the attached illustrations.

DETAILED DESCRIPTION OF THE INVENTION

Figure 1:
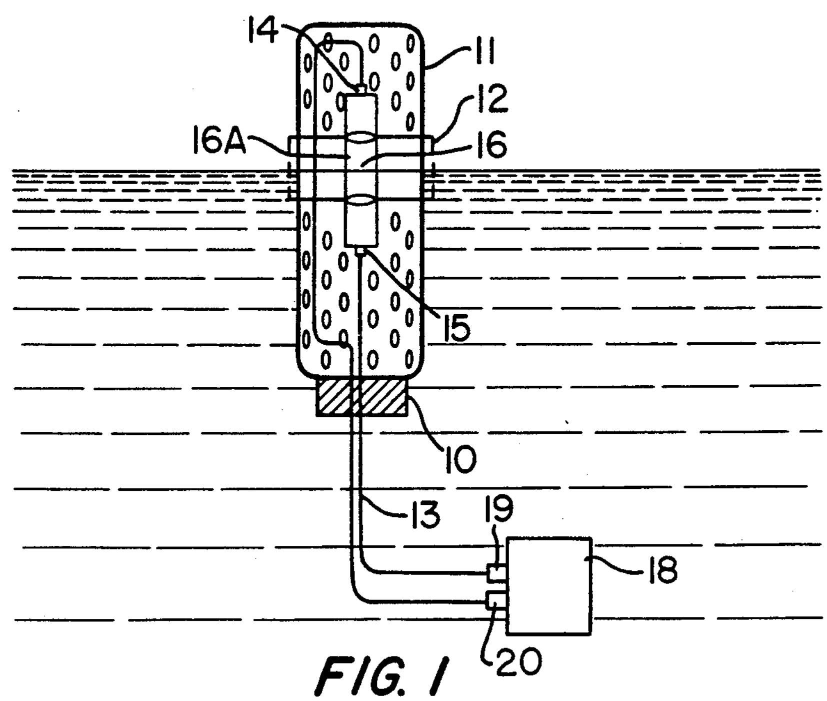
FIG. 1 Illustrates a vertical cross section of a floating sensor buoy using an Intensity Sensor provided with lenses.

FIG. 1 illustrates a control system having a sensor unit in form of a floating buoy 11 contained in a protective stainless steel net 12. The buoy 11 is anchored by some means to a firm position at sea.

The duplex optical fiber cable 13 is connected to a distant control box 18 situated in the control center in the port or wherever required.

Figure 2:
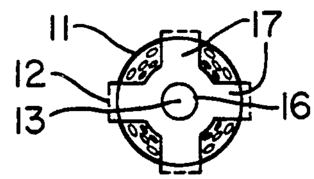
FIG. 2 Illustrates a horizontal cross section of the central part of a floating sensor buoy.

The control box 18 contains in it an alarm unit, an electronic processing unit, including a microprocessor and software. A light emitter 19 is attached to one end of the fiber and a light detector receiver 20 is connected to the other end of the fiber, of the cable 13. The buoy 11 has a central sensing position bore 16, which is adjusted so that the central part of the sensor (indicator) 16A is positioned at sea level by a weight 10. The details of the bore can be seen in FIG. 2 which is a cross section of the buoy at the floating position. The channels 17 lead concentrically to the sensing position 16. At the sensing position 16 the optical fiber in cable 13 is terminated, and one fiber end 14 is placed on top of the sensing position 16, and the other fiber end 15 is placed on the bottom thus forming a gap into which sea water flows through the channels 17. Two lenses are mounted on the two fiber endings 14, and 15. The size of the lenses is adjusted to the numerical aperture of the fibers. So that when an oil spill enters the gap between the lenses, the detector 20 records the reduced light intensity caused by the absorption and scattering, and supplies the information to the electronic processing unit, and when it detects a reduction in the light intensity, due to differential absorption and scattering of the light by an oil slick, excluding the effect caused by waves motion, the electronic processing unit sets on the alarm provided in the control box 18.

Figure 3:
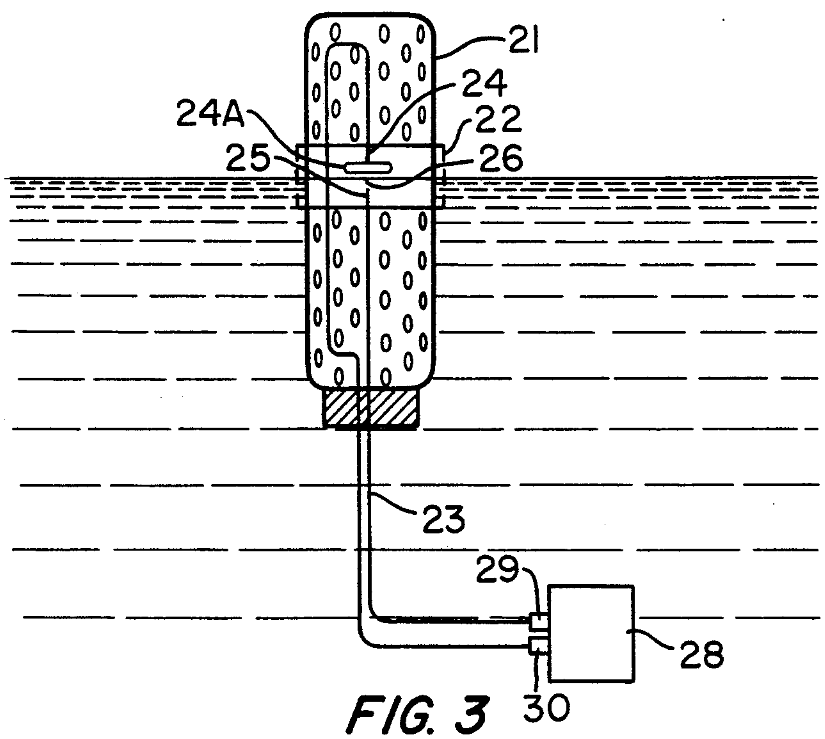
FIG. 3 Illustrates an alternative embodiment of the floating sensor buoy using the Intensity Sensor with one lens only.

FIG. 3 illustrates an alternative embodiment having one lens only.

The buoy 21 contains the stainless steel net 22. The optical cable 23 enters into the sensing position 26 at sea level, where the optical fiber is terminated, and one fiber end 24 is placed on top of position 26, and the other fiber ending 25 is placed on the bottom. The first fiber end 24 is provided with a lens 24A. The optical cable 23 is connected at the other end to a control box 28 placed at the control center. The control box 28 is provided with alarm means, and an electronic processor. One fiber ending is connected to a light emitter 29, and the other ending to a light detector 30.

When clear sea water enters through the channels 27 to the sensing position gap 26, a level of the light intensity is recorded, and when the water is contaminated with oil the intensity changes drastically, and the electronic processor in the control box 28 sets on the alarm.

The effects on the light intensity caused by displacement and tilting movement of the water level with respect to the optical axes of the fibers are compensated by the microprocessor, and suitable software.

Figure 4:
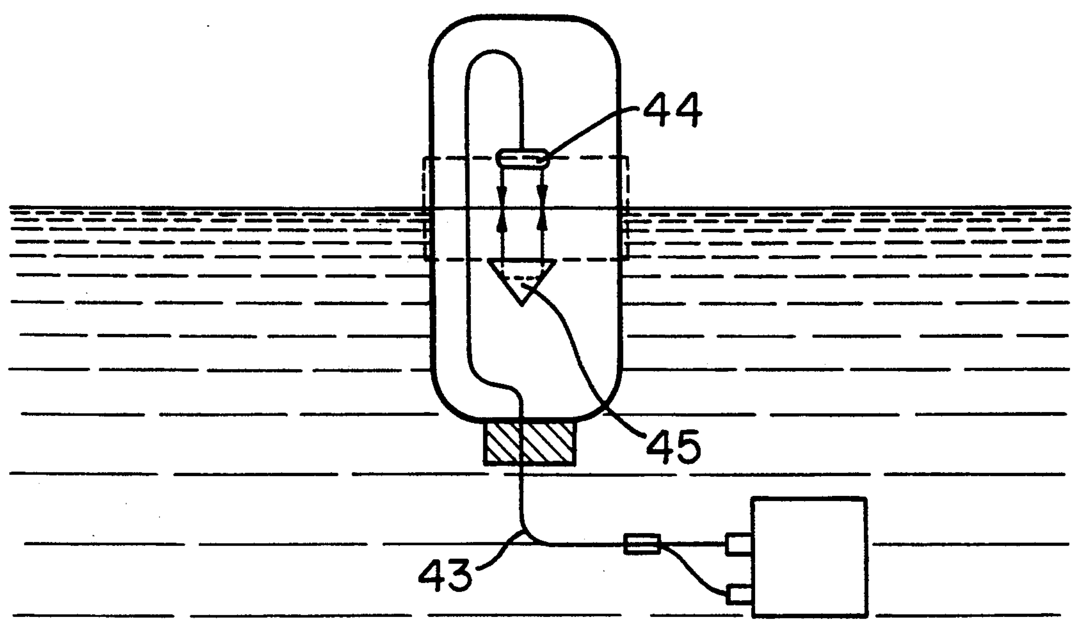
FIG. 4 Illustrates an alternative embodiment of the floating sensor buoy with the use of a simplex cable and an optical prism.

FIG. 4 illustrates an alternative embodiment having a simplex cable 43, one lens 44 and an optical prism 45. Most of the light is refracted back from the prism 45 to the lens 44, even when the water surface tilts with reference to the optical axis of the fiber. This happens due to a proper numerical aperture of the lens 44 as well as proper geometrical dimension of the optical prism 45 and its location with respect to the lens 44.

Figure 5:
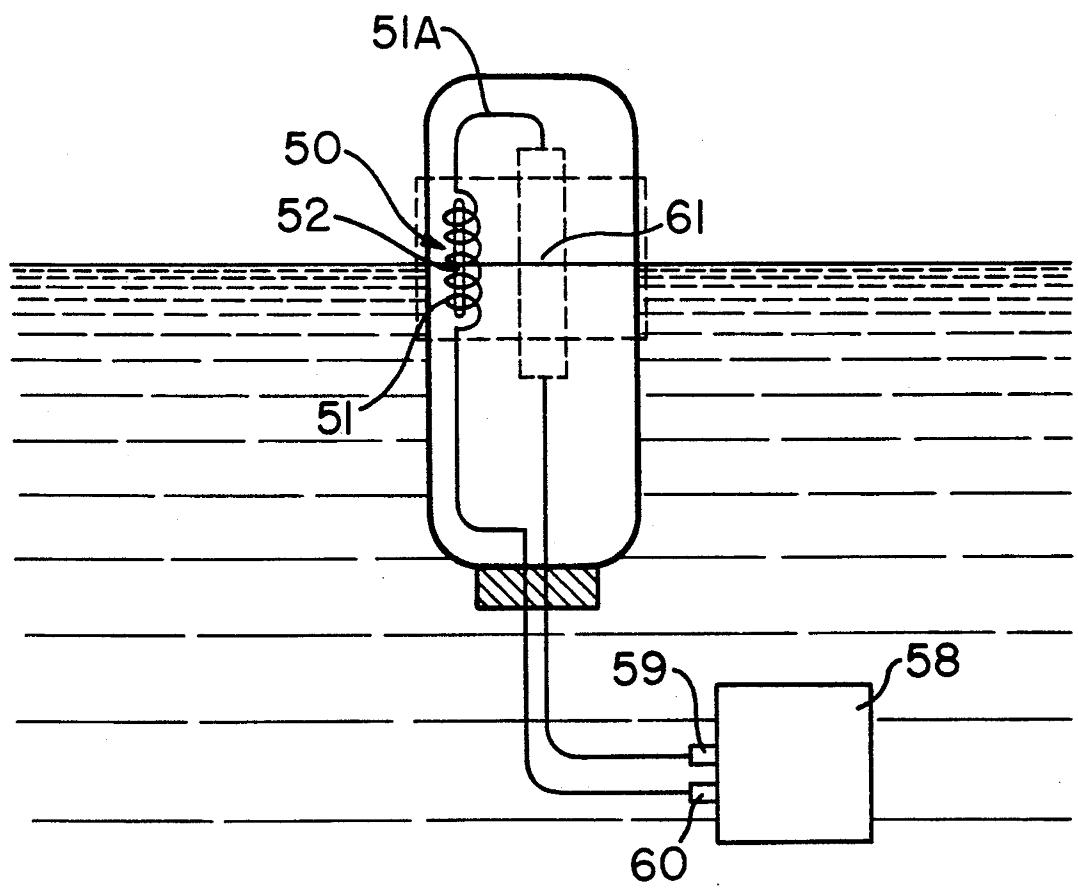
FIG. 5 Illustrates an alternative embodiment of the floating sensor buoy, using Refractive Index Sensor on its own or in combination with any Intensity Sensors, shown in FIGS. 1, 3, 4.

FIG. 5 illustrates another embodiment of the floating sensor buoy, having a Refractive Index (RI) sensor 50. RI sensor 50 is located at the water level, vertically along the central bore of the buoy. RI sensor 50 comprises a noninsulated metal coated optical fiber 51, coiled around a circular bar 52. The bar 52 has a diameter small enough to cause the transmitted light power to leak by scattering from the fiber's 51 core to its surrounding clad. The fiber clad is coated by a thin metal layer of platinum, gold, palladium or rhodium in order to mechanically protect the clad, as well as to increase its sensitivity to the change of the refractive index of the surroundings and consequently of the internal refraction angle from the outside surface of the clad, caused by the contaminated water. Once oil is present near the coil 51, the leakage of light from the clad caused by the oil contamination results in reducing of the light power received, and the electronic processor in the control box 58 sets on the alarm.

The fiber 51A returning from the RI sensor 50 may go uninterrupted through a detector 60 to the control box 58, or may have on its returning loop any of the Intensity sensors 61, shown in FIGS. 1, 3, 4. When the oil is present at the water level, it will amplify the loss of the light power, and the system will be more sensitive.

The invention has been described in reference to the attached drawings, it should be appreciated that several other embodiments of the optic cable the, sensor unit, the buoy, or the control box are possible and they should all be considered as being part of this invention.

I claim:

1. An automatic detection system for control of oil spillage into sea waters comprising a plurality of optical fiber cables connected each at the first ending to a control box having an electronic processing and alarm means, and a plurality of light transmitters and light detectors connected to said first endings of said optical fiber cables; and the second endings of said fiber cables are connected to a plurality of sensors located remotely in the open sea; and each of said sensors is a part of a closed loop of a light signal transmitted by one of said light transmitters through one of said optical fiber cables through said sensor, and received by one of said light detectors provided in said control box; and each of said sensors consists of a floating buoy affixed by mechanical means to a permanent location in the open sea, so as to allow said buoy free vertical movement but limit its horizontal movement; and said buoy is constructed of a light weight floatable material, and has its center of gravity adjustable and stabilized by a weight, so that when it floats, the central part of said sensor rests at sea level and said buoy is provided with a central bore, into which said second optical fiber cable's ending is positioned; and a plurality of concentric channels are provided from all sides of said bore, leading sea water from the outer surface of said buoy inwards; and said second optical fiber cable's ending is terminated in said bore and provided with a light indicator; so that said light signal, transmitted through said optic fiber cable form said light transmitter, passes through said light indicator and when an oil slick enters said bore, the light parameters' change can be instantaneously detected by said light detector and said electronic processing means of said control box set on said alarm means.

2. The detection system as in claim 1, wherein said light indicator contains a light intensity sensor, comprising two fiber ends placed one opposite the other in said bore, so that one fiber end is positioned below sea level and the other is placed above sea level; and when said light signal passes through a gap formed between said two fiber ends, light absorption and dispersion through said oil slick, sea water and air is higher than the light absorbed through the sea water and air only; and said differential light absorption can be instantaneously detected by said light detector.

3. The detection system as in claim 1, wherein said optical fiber cable consists of a single fiber, and said light indicator is a light intensity sensor, provided with a reflector located in a position so as to create a gap between said fiber's end and said reflector; and said reflector reflects back into said fiber the light transmitted through said fiber's first end; and on said second end of said fiber an optical coupler is provided transmitting the reflected light beam into a receiver which detects the differential light absorption caused due to interference of an oil slick; and said electronic processing means then set on the alarm.

4. The detection system as in claim 1, wherein said light indicator contains a refractive index sensor, comprising a noninsulated optical fiber of said optical fiber cable; said fiber passes in said bore at sea level, and said fiber is coiled around a circular bar and its core is surrounded with a clad, capable to transmit a light energy, leaking from the core of said optical fiber, caused by the coiling; and said clad is coated along said coil by a thin metal layer; and said clad changes its light transmission properties according to changes in the refractive index of its surrounding medium; so that, when the surrounding waters are contaminated with organic oils, the refractive index of said surrounding medium increases, thus some of the light power leaking from said core is transmitted in said clad and is leaded into said surrounding medium, hence a reduction of the light power can be instantaneously detected by said light detector.

5. The detection system as in claim 1, wherein said light indicator contains both said light intensity sensor, and said refractive index sensor, connected in sequence and acting as amplifiers to each other.

6. The detection system as in claim 4, wherein said optical fiber is made of a plastic clad silica; and said plastic clad is removed along said coiled fiber; and said metal layer is applied directly on said optical fiber's core.

7. The detection system as in claim 4, wherein said metal layer is of platinum, rhodium, gold or palladium.

8. The detection system as in claim 3, wherein said reflector is a mirror or an optical prism.

9. The detection system as in claim 2, wherein said light indicator does not include any optical auxiliary device, and said fiber ends are spaced at a close distance between each other, the preferred gap should not exceed 100 mms.

10. The detection system as in claim 2, wherein at least one of said two fiber ends is connected to a lens which size, curvature and focal length are preferably adjusted to the location and the numerical aperture of said fiber, for said lens to be optimally illuminated.

11. The detection system as in claim 2, wherein said two fiber ends forming the indicator's gap are each connected to a plurality of lenses arranged consequently, so that the light energy transmitted from said one fiber end is collected effectively through said lenses of said other fiber end.

12. The detection system as in claim 2, wherein said lenses are constructed of a special plastic or glass grade, so chosen to maximize the light energy transmitted from the one lens connected to said one fiber ending to the other lens connected to said other fiber end in said indicator's gap.

13. The detection system as in claim 2, wherein said lenses and fiber are coated with a special coating so chosen to maximize the light energy transmitted from the one lens connected to said one fiber end to the other lens connected to said other fiber end in said indicator's gap; and said coating is capable to repeal oil to prevent it from sticking to the optical surfaces.

14. The detection system as in claim 1, wherein said electronic processing means are provided with software, capable to differentiate light loss created by the motion of sea waves, and light absorption created by the oil slick, thus providing an accurate control of said alarm means.

15. The detection system as in claim 1, wherein said optical fibers are protected in a single or multi cable system.

16. The detection system as in claim 1, wherein said cable is a duplex fiber cable, having two fibers only.

17. The detection system as in claim 1, wherein said cable is a multifiber cable.

18. The detection system as in claim 1, wherein said optic fiber cable is made of all glass fibers.

19. The detection system as in claim 1, wherein said cable is made of plastic coated glass fiber.

20. The detection system as in claim 1, wherein said cable is made of all plastic fiber.

21. The detection system as in claim 1, wherein said fiber is a single mode type.

22. The detection system as in claim 1, wherein said fiber is a multimode type.

23. The detection system as in claim 1, wherein said fiber is a step index type.

24. The detection system as in claim 1, wherein said cable is a submarine cable type.

25. The detection system as in claim 1, wherein said light wavelength applied in said system should be 820 nm.

26. The detection system as in claim 1, wherein said light transmitted emits pulsed light with predetermined duration and intervals so that the detection may be recognized efficiently by said electronic processing unit installed in said control box.

27. The detection system as in claim 1, wherein said buoy is inserted in a cage which is connected to a fixed structure built out at sea, or is anchored by any commercial anchor means; and said cage affixes said buoy movement allowing it to move vertically free, but limiting its horizontal movement.

28. The detection system as in claim 1, wherein said cage is connected to an anchoured mooring buoy.

29. The detection system as in claim 1, wherein said floating buoy containing said light indicator has a stainless steel net cover preventing the passage of sea weeds, fish or other solid polluants into said buoy concentric channels leading to said bore, wherein said optical fibers are placed.

30. The detection system as in claim 1, wherein said buoy is provided with a dispenser releasing a chemical preventing the build up of bacteria or sea weeds in said buoy channels leading to said bore, and on said light indicator's optical surfaces.

31. The detection system as in claim 1, wherein said light indicator's optical surfaces are coated with an oil repelling layer, repelling oil from sticking to said surfaces.

32. The detection system as in claim 1, wherein said buoy is made of foamed light weight material such as cork, or any other foamed plastic material commercially used in sea floats, such as polystyrene, polyurethane, polyethylene or the like, protected by a suitable protective layer, such as paint or a protective chemical varnish.

33. The detection system as in claim 1, wherein said buoy is stabilized by fins so that the axis of the light rays transmitted through said fiber ends in said light indicator, are always emitted in an almost perpendicular angle to the water level, regardless of effects by sea waves.

34. The detection system as in claim 1, wherein said buoy contains wave breakers in the form of mechanical hurdles which eliminate the surface roughness of the water entering said light indicator's gap, thus keeping the water level in said sensor's gap as calm as possible.

* * * * *